United States Patent [19]

Lyons et al.

[11] Patent Number: 4,906,385
[45] Date of Patent: * Mar. 6, 1990

[54] METHOD FOR CONTROLLING MACROINVERTEBRATES

[75] Inventors: Larry A. Lyons, Woodbury, N.J.; Dwight P. Davis, Newtown; Paul Swered, Philadelphia, both of Pa.

[73] Assignee: Betz Laboratories, Inc., Trevose, Pa.

[*] Notice: The portion of the term of this patent subsequent to May 31, 1988 has been disclaimed.

[21] Appl. No.: 305,231

[22] Filed: Feb. 1, 1989

Related U.S. Application Data

[63] Continuation of Ser. No. 135,503, Dec. 18, 1987, Pat. No. 4,816,163, which is a continuation of Ser. No. 889,446, Jul. 23, 1986, abandoned.

[51] Int. Cl.$^4$ ................................................ C02F 5/00
[52] U.S. Cl. .................................... 210/698; 210/749; 210/764; 514/634; 106/18.32
[58] Field of Search ............... 210/698, 249, 764, 755; 514/634, 643, 515; 106/18.32

[56] References Cited

U.S. PATENT DOCUMENTS

| | | | |
|---|---|---|---|
| 2,409,883 | 10/1946 | Migrdichian | 167/37 |
| 2,906,595 | 9/1959 | Pelcak et al. | 21/2.7 |
| 3,090,723 | 5/1963 | Pastac | 210/764 |
| 3,142,615 | 7/1964 | Wehner | 167/22 |
| 3,231,509 | 1/1966 | Shema | 210/764 |
| 3,264,172 | 8/1966 | Regutti | 162/161 |
| 4,328,638 | 5/1982 | Smithson | 43/124 |
| 4,462,914 | 7/1984 | Smith | 210/755 |
| 4,561,983 | 12/1985 | Davis et al. | 210/755 |
| 4,579,665 | 4/1986 | Davis et al. | 210/755 |
| 4,745,132 | 5/1988 | Swered et al. | 514/643 |
| 4,789,489 | 12/1988 | Hollis et al. | 210/764 |
| 4,816,163 | 3/1989 | Lyons et al. | 210/698 |

OTHER PUBLICATIONS

"Bivalve Fouling of Nuclear Power Plant Service-Water Systems", U.S. Nuclear Regulatory Commission 1984 Report.
"Freshwater Macrofouling and Control with Emphasis on Corbicula", Dec. 1983 Proceedings of Electric Power Research Institute.
"Clams—A Growing Threat to Inplant Water Systems", Plant Engineering, Jun. 1979, p. 165.
"Interactions of Corbicula sp. with Power Plants", Mattice, J. S., 1979, pp. 119–138 in: Proceedings, First International Corbicula Symposium, J. C. Britton (Ed.), Texas Christian University Research Foundation, Fort Worth, Texas, 313 pages.
"Control Studies on Corbicula for Steam Electric Generating Plants", Goss, L. B. et al., 1979 in: Proceedings, First International Corbicula Symposium, J. C. Britton (Ed.), Texas Christian University Research Founcation, Fort Worth, Texas, 313 pages.
"What Are We Doing About the Asiatic Clam?", Power, Jan. 1982.
Preamble to Steam Electric Power Generating Point Source Category Effluent Limitation Guidelines (47 FR 52290).
"Corbicula Variation and Dreissena Parallels", The Biologist, vol. 53, No. 3, Aug. 1971, pp. 153–159.
"Thermal Tolerance of the Adult Asiatic Clam Corbicula Manilensis", Mattice & Dye, Proceedings of Second Thermal Ecology Symposium, Apr. 1975.
"Procedures for Evaluating Chemical Control of Larval Asiatic Clams", Foster & Bok.
Untitled Paper (18 pp.) on "Asiatic Clams . . . " with Bibliography.
21 CFR 176.170.
Cytox 2013 Industrial Microbiocide Fact Sheets.
Cytox 2013-P Material Safety Data Sheets.
Cytox 2014 Label.
21 CFR 176.300.
Hyamine 3500 Product Information Sheets.

*Primary Examiner*—W. Gary Jones
*Attorney, Agent, or Firm*—Alexander D. Ricci; Roslyn T. Tobe

[57] ABSTRACT

A method of controlling the fouling potential of macroinvertebrates, such as mollusks, in aqueous systems which comprises adding to the system an effective controlling amount of a water-soluble alkyl guanidine salt wherein the alkyl group has from about 8 to about 18 carbons.

27 Claims, No Drawings

METHOD FOR CONTROLLING MACROINVERTEBRATES

This is a continuation of application Ser. No. 135,503 filed on Dec. 18, 1987, now U.S. Pat. No. 4,816,163, which is a continuation of Ser. No. 889,446 filed July 23, 1986, now abandoned.

BACKGROUND OF THE INVENTION

This invention relates to the control of fouling by macroinvertebrates, especially mollusks, in aqueous systems by utilizing a water-soluble alkyl guanidine salt wherein the alkyl group has from about 8 to about 18 carbons.

More particularly, this invention relates to control of potential macroinvertebrate fouling in cooling systems for both industrial plants and utilities which are subject to such fouling, whether the system is using cooling water on a once-through basis or is of the recirculating type. The once-through systems operate by drawing cooling water through the process to be cooled on a one-time basis and discharge the water directly to the receiving body with a short residence time (usually minutes to hours), whereas recirculating cooling systems require the addition of only a fraction of the system volume as makeup water. Additionally, the service water systems (waste, safety and auxiliary cooling) which are often a part of these cooling systems are also quite vulnerable to macroinvertebrate fouling, primarily because they do not run continuously, the conduits are of a smaller diameter, and more time is allowed for macroinvertebrate growth.

The extent and type of macroinvertebrate fouling will depend upon many factors such as the source of the cooling water, the season, the water temperature, the growth rate of the fouling macroinvertebrate, and the linear velocity of the cooling water. Because of the large quantities of cooling water used, the locality of the plant will dictate the water's source. A fresh water cooling system will be drawing from a river, lake or well, whereas plants situated along coastal areas will most likely utilize brackish or marine water for their systems.

Both once-through and recirculating types of cooling water are treated prior to entering the system by screening to remove objects which are large enough that they could damage pumps and heat exchange equipment. This screening does not prevent the passage of the early life-stages or larval stages of the macroinvertebrates, which are the precursors to fouling as growth conditions are usually favorable within these systems. These early life stages of the macroinvertebrates will settle out in low flow areas or attach to substrate within the cooling system and grow to mature organisms.

For example, mollusks are common macroinvertebrates which can cause macrofouling problems to marine and fresh water cooling systems. Macrofouling by mollusks, like other groups of macrofouling macroinvertebrates—barnacles, bryozoans, sponges, hydroids, tunicates and annelids—is initiated by the settlement or attachment of larval and/or juvenile stages that are easily entrained by the service waters of cooling systems. Fouling caused by the settlement, attachment and/or biogrowth of the mollusks in the cooling systems and associated service water systems of the industrial plants and utilities which utilize large quantities of water is a major problem causing a variety of deleterious effects to the structure, operation and safety of these systems. As indicated in the U.S. Nuclear Regulatory Commission 1984 Report entitles "Bivalve Fouling of Nuclear Power Plant Service—Water Systems", the safe operation of a nuclear power plant is a concern because of fouling caused by the Asiatic clam (*Corbicula fluminea*), the blue mussel (*Mytilus edulis*) and the American oyster (*Crassostrea virginica*). This report describes the correlations between the biology of these bivalve mollusks and the design and operation of power plants that allow bivalves to enter and reside within their cooling water systems.

One of the species of mollusks controlled by the method of this invention is the Asiatic clam, Corbicula spp. As indicated in the article entitled "Freshwater Macrofouling and Control with Emphasis on Corbicula" in the December 1983 Proceedings of the Electric Power Research Institute (EPRI), the Asiatic clam has caused significant incidents of macrofouling to fresh water cooling systems of power plants. Another freshwater mollusk, Dreissena spp—the Zebra mussel, causes fouling problems in Europe to cooling systems in a similar manner as the Asiatic clam. Both Dreissena and Corbicula have free floating planktonic veliger larvae which allow easy penetration into cooling systems. Similar macrofouling problems plague cooling systems using estuarine or marine waters, but with different species of macroinvertebrates.

As a specific example of how a macroinvertebrate can cause fouling problems, a description of some characteristics of the Asiatic clam follows:

One-year-old clams are capable of plugging valves and nozzles. Two-year-old clams can cause mechanical damage to impellers and other moving parts of water-distribution systems. At six years, the clam can damage tires of construction vehicles. As in all other clams, growth is rapid in early years and then tapers off. "Clams—A Growing Threat to Inplant Water Systems", *Plant Engineering,* June, 1979, p. 165.

The Asiatic clams are very tolerant of many chemicals and often occur in great abundance. They have accumulated to depths of two meters in the Delta-Mendota Canal in California and have caused reduction in water flow. Some industrial plants have had difficulty obtaining fire insurance after inspectors found the fire protection systems plugged with Corbicula shells. Pump impellers have been damaged by shells in some industrial plants. The number of power plants which have experienced problems with this species has been steadily increasing during the past several years. Problems in fossil-fueled power plants most often relate to pluggage of condenser tubes, surface water heat exchangers, and blockage of fire protection systems. In addition to these problems, nuclear power plants may have other problems associated with the shutdown service water, and emergency reactor cooling systems. For further information, see also Mattice, J. S., 1979. "Interactions of Corbicula sp with Power Plants", pages 119–138 and Goss, L. B. et al., 1979, "Control Studies on Corbicula for Steam Electric Generating Plants", pages 139–151, in J. C. Britton (ed), Proceedings, First International Corbicula Symposium, Texas Christian University Research Foundation, Fort Worth, Texas, 313 pages.

Fouling control of macroinvertebrates, such as mollusks, has been attempted using physical/mechanical and chemical techniques (see, e.g., U.S. Pat. No. 4,328,638), but no foolproof combination has been developed. For example, chlorine, which has been by far the most used biofouling control agent, has several limitations: prolonged exposures are required to achieve efficacy, chlorine demand of the cooling water reduces its potency, and strict environmental regulations are being imposed which act to severely limit the discharge of chlorine residues, and in some cases seek to eliminate its use altogether.

In addition to chlorine, Smith, U.S. Pat. No. 4,462,914 discloses the use of a high density cationic polymer to control Corbicula. While the polymer appears to be efficacious toward the adult clam after a six day exposure period, it suffers from some of the same drawbacks as chlorine.

The above-mentioned concerns over potential fouling biocides is well described by the following excerpt from the December 1983 Proceedings of the Electric Power Research Institute:

"Chemical controls have an inherent liability. What can kill inside the power plant may also impact the receiving water body: chemical toxicants are not specific. The perfect chemical would be stable enough to be effective inside the plant, but become non-toxic, via chemical reaction or decay, before or as it entered the receiving water body. So far, no chemical meets these specifications: chlorine and bisulfate/sulfide which have actually been used in an attempt to control Corbicula fouling have not been effective alone or have been successful only under limited conditions. Such a chemical may not exist, but scheduling of application of a chemical at the beginning of scheduled outages may offer a less stringent alternative, because of the possibility of extending holdup times."

U.S. Pat. No. 4,561,983 discloses the use of a nitrostyrene compound to control the fouling potential of mollusks. U.S. Pat. No. 4,579,665 discloses the use of a nitrostyrene compound and an alkyl thiocyanate compound to control mollusk fouling potential. Also, the compound of the present invention has been utilized for control of microorganisms, i.e., bacteria, fungi, and algae, but has not been suggested for control of larger, more complex organisms, especially macroinvertebrates, in aqueous systems. See, e.g., U.S. Pat. Nos. 2,906,595 and 3,142,615, and 21 CFR 176.170. Bacteria, fungi and algae microorganisms are dependent upon the presence of metabolizable components in an aqueous system. However, the presence or absence of macroinvertebrates, such as mollusks, is essentially independent of the presence of metabolizable components in the water because they are much more complex organisms than microorganisms, both in terms of anatomic and physiological complexity and position in the food chain. Macroinvertebrates, such as mollusks, are unable to exist on metabolizable components. Rather, macroinvertebrates require small plants or animals as foodstuff. Until the unexpected discovery of the applicants, the use of the compound of the present invention has never before been appreciated to control macroinvertebrates.

SUMMARY OF THE INVENTION

This invention relates to a method for controlling the fouling potential of macroinvertebrates, especially mollusks such as the Asiatic clam, in an aqueous system which comprises adding to the system an effective controlling amount of a water-soluble alkyl guanidine salt wherein the alkyl group has from about 8 to about 18 carbons. Preferably, the water-soluble alkyl guanidine salt is n-dodecylguanidine hydrochloride.

DETAILED DESCRIPTION OF THE INVENTION

The present inventors discovered that the survival of juvenile and adult macroinvertebrates, particularly veliger stage mollusks and adult mollusks, in an aqueous system could be significantly impaired by adding to the system a sufficient amount for the purpose (depending upon the severity or potential severity of the problem) of an effective water-soluble alkyl guanidine salt wherein the alkyl group of the salt has from about 8 to about 18 carbon atoms. Exemplary alkyl guanidine salts that may be used include the water-soluble hydrochloride, hydrobromide, sulfate, bisulfate, acetate, carbonate and nitrate salts. Preferably, the water-soluble alkyl guanidine salt is n-dodecylguanidine hydrochloride, which is presently commercially available under the trademark "Cytox 2013" or "Cytox 2014" from American Cyanamid.

Veliger stage and adult mollusks which are particularly affected by the compound are the Asiatic clams, more specifically Corbicula spp. However, it is believed that not only mollusks, but also macrofouling macroinvertebrates, can be controlled in accordance with this invention. The term "macroinvertebrate" as used herein is defined as the range of aquatic organisms that develop from a juvenile or larval life stage form to adult life stage forms. Macroinvertebrates are complex multi-cellular organisms containing an integration of organs and tissues that make up advanced life support systems (i.e., circulatory, digestive, reproductive, nervous . . . ). Macroinvertebrates often require the availability of microorganisms for providing the energy source for their sustenance. It is the result of the development of the adult life stages of macroinvertebrates that can cause many unique fouling problems to cooling systems categorized under the term "macrofouling" (i.e., damaging equipment, jeopardizing safety related systems, reducing line pressure that can reduce cooling efficiency, and reducing cooling efficiency can jeopardize the system's equipment and reduce overall efficiency and revenue). Exemplary macroinvertebrates include mollusks (i.e., clams, mussels, oysters, and snails), crustaceans (i.e., barnacles), sponges, annelids, bryozoans and tunicates.

In accordance with the present invention, the alkyl guanidine salt treatment may be added to the desired aqueous system in need of macrofouling control, in an amount from about 0.1 to about 1000 parts of the treatment to one million parts (by weight) of the aqueous system to be treated. Preferably, about 0.1 to about 100 parts of the treatment to one million parts (by weight) of the aqueous medium is added.

Methylene bis-thiocyanate and/or water soluble alkyl dimethyl benzyl ammonium chloride with alkyl chain lengths of $C_6$ to $C_{24}$ (hereinafter sometimes referred to as Quat), such as n-alkyl (50% $C_{14}$, 40% $C_{12}$, 10% $C_{16}$) dimethyl benzyl ammonium chloride, which has been found to be effective in controlling macrofouling macroinvertebrates, may be combined with the water-soluble alkyl guanidine salt in order to provide a commercially attractive macroinvertebrate control treatment product. N-alkyl (50% $C_{14}$, 40% $C_{12}$, 10% $C_{16}$) dimethyl benzyl ammonium chloride is commercially available from various sources. For instance, it is presently sold under the trademark "Maquat 1412" from Mason Chemical Co., "Onyx 8358" from Onyx Chemical Co., or "Hyamine 3500" from Lonza, Inc. It is desirable to add such methylene bis-thiocyanate and/or Quat to the aqueous system in an amount of from about 0.1 ppm to about 1000 ppm, with 0.1 ppm to 100 ppm being preferred.

This invention can be used to control potential macroinvertebrate fouling in cooling systems for both industrial plants and utilities which are subject to such fouling, whether the system is using cooling water on a once-through basis or is of the recirculating type. This invention can also be used to control all life stages of the macroinvertebrates. For example, addition of n-dodecylguanidine hydrochloride in an effective amount to the incoming water of a once-through cooling system to destroy planktonic juveniles before such settle and form the adult clam or mollusks, provides adequate inhibition of clam infestation and the consequent build-up in the structural parts of the cooling water system. Furthermore, the destruction of adult clams could also be accomplished to eradicate fouling problems of a more mature nature.

While other biocidal materials do have some efficacy, for instance, chlorine, chlorophenates, cationic polymers, and the like, these chemicals require long exposure periods to the macrofouling organism to achieve control. The present inventors, in reviewing the Asiatic clam problem, were attempting to discover chemicals which would not only be effective in controlling macroinvertebrates, especially mollusks, but which would be effective with shorter exposure periods. Subsequently, reduced exposure periods of the chemicals to the cooling systems will provide not only a more economical means of treating the cooling systems, but also lessen the potential environmental concerns. Furthermore, the inventors were in search of chemicals that could be altered or neutralized during the application process to products that would cause less environmental concern by the natural constituents present in the cooling systems. There are many agents (for instance bacteria and other microorganisms, silt, clays, humic and organic acids, plus other anionic materials and polymers) which would provide assistance in neutralizing and eliminating toxic effects of the compounds prior to being discharged. The present inventors found that the water-soluble alkyl guanidine salt of this invention, in fact, provides all of these properties. Furthermore, it was discovered that this compound provides an unexpected latent efficacy response in controlling the macroinvertebrates. By the terms "latent efficacy response", it is meant that an effective response of reducing the presence of macrofouling organisms is initiated or apparent at a period of time after the biocide exposure. In the examples provided herein, the latent efficacy response was defined by mortality of mollusks following biocide treatment periods.

The following examples are provided to illustrate preferred embodiments of the invention and are not intended to restrict the scope thereof.

EXAMPLE 1

Static renewal tests were conducted with fresh aqueous solutions prepared daily at 0 hours, 24 hours, 48 hours, and 72 hours. At 96 hours the recovery period was initiated by the exchange of the test solution with fresh culture water to monitor the latent efficacy responses. The test organisms were adult Asiatic clams (one year olds) with a size range of 7.5–11 mm. Each test solution was run in replicate (2) with 6 clams per replicate. Mortality was determined when the bivalve shell gaped open. The results are reported in Table I.

EXAMPLE 2

Static renewal tests were conducted as described in Example 1 using adult Asiatic clams (one year olds) with a size range of 7–12.5 mm. However, one test solution was exposed to the clams for only a 24 hour period followed by a latent efficacy evaluation. The results are reported in Table II.

EXAMPLE 3

Naturally spawned veliger larvae were collected from adult Corbicula, which were collected from a tributary of the Delaware River, Mercer County, NJ. Larvae released by the gravid clams during the 24 to 48 hour period following collection were transferred to culture dishes until testing was initiated. The larvae being released during this period were microscopically examined and confirmed to be in the late veliger stages: possession of a fully developed foot, a completely developed bivalve shell encasing all soft body tissues, and a reduced or absent velum. Only late stage veliger larvae exhibiting active foot and shell movements and ciliary activity were retained for testing.

TABLE I

| Actives | Total Active Concentration | Percent Mortality | | | | | | | Latent Response 120 Hr. |
|---|---|---|---|---|---|---|---|---|---|
| | | 24 Hr. | 42 Hr. | 48 Hr. | 66 Hr. | 72 Hr. | 90 Hr. | 96 Hr. | |
| Control | 0 mg/l | 0 | 0 | 0 | 0 | 0 | 0 | 0 | 0 |
| DGH | 0.625 mg/l DGH | 0 | 0 | 0 | 0 | 25 | 58 | 67 | 83 |
| DGH | 1.25 mg/l DGH | 0 | 0 | 0 | 58 | 83 | 92 | 100 | 100 |
| DGH | 2.5 mg/l DGH | 0 | 0 | 0 | 58 | 75 | 100 | 100 | 100 |
| DGH | 5.0 mg/l DGH | 0 | 0 | 25 | 100 | 100 | 100 | 100 | 100 |
| MBT | 0.625 mg/l MBT | 0 | 0 | 0 | 0 | 0 | 33 | 42 | 100 |
| MBT | 1.25 mg/l MBT | 0 | 0 | 0 | 0 | 0 | 33 | 50 | 92 |
| MBT | 2.5 mg/l MBT | 0 | 0 | 0 | 0 | 17 | 100 | 100 | 100 |
| MBT | 5.0 mg/l MBT | 0 | 0 | 17 | 42 | 58 | 100 | 100 | 100 |
| Quat | 0.625 mg/l Quat | 0 | 0 | 0 | 0 | 8 | 83 | 92 | 100 |
| Quat | 1.25 mg/l Quat | 0 | 0 | 0 | 50 | 58 | 92 | 92 | 100 |
| Quat | 2.5 mg/l Quat | 0 | 0 | 0 | 92 | 92 | 100 | 100 | 100 |
| Quat | 5.0 mg/l Quat | 0 | 0 | 0 | 83 | 83 | 100 | 100 | 100 |
| MBT:DGH | 2.5 mg/l MBT:.625 mg/l DGH | 0 | 75 | 100 | 100 | 100 | 100 | 100 | 100 |
| MBT:DGH | 2.5 mg/l MBT:1.25 mg/l DGH | 0 | 17 | 25 | 83 | 100 | 100 | 100 | 100 |
| MBT:DGH | 2.5 mg/l MBT:2.5 mg/l DGH | 0 | 8 | 17 | 58 | 83 | 92 | 92 | 100 |
| MBT:DGH | 1.25 mg/l MBT:2.5 mg/l DGH | 0 | 0 | 17 | 75 | 92 | 92 | 100 | 100 |
| MBT:DGH | .625 mg/l MBT:2.5 mg/l DGH | 0 | 0 | 17 | 50 | 75 | 83 | 83 | 92 |

TABLE I-continued

|  |  | Percent Mortality | | | | | | | Latent Response 120 Hr. |
|---|---|---|---|---|---|---|---|---|---|
| Actives | Total Active Concentration | 24 Hr. | 42 Hr. | 48 Hr. | 66 Hr. | 72 Hr. | 90 Hr. | 96 Hr. | |
| MBT:BNS | 2.25 mg/l BNS:1.25 mg/l MBT | 0 | 58 | 58 | 92 | 92 | 100 | 100 | 100 |
| DGH:Quat | 2.0 mg/l Quat:1.25 mg/l DGH | 0 | 0 | 0 | 67 | 75 | 100 | 100 | 100 |
| MBT:DGH:Quat | 1.25 mg/l MBT:.625 mg/l DGH:1.25 mg/l Quat | 0 | 0 | 17 | 83 | 100 | 100 | 100 | 100 |

DGH = n-dodecylguanidine hydrochloride
MBT = methylene bis-thiocyanate
Quat = n-alkyl (50% $C_{14}$, 40% $C_{12}$, 10% $C_{16}$) dimethyl benzyl ammonium chloride
BNS = beta-bromo-beta-nitrostyrene

TABLE II

|  |  | Percent Mortality | | | | | | | Latent Response | | | |
|---|---|---|---|---|---|---|---|---|---|---|---|---|
| Actives | Total Active Concentration | 24 Hr. | 41 Hr. | 48 Hr. | 65 Hr. | 72 Hr. | 89 Hr. | 96 Hr. | 114 Hr. | 163 Hr. | 170 Hr. | 185 Hr. |
| Control | 0 mg/l | 0 | 0 | 0 | 0 | 0 | 0 | 0 | 0 | 0 | 0 | 0 |
| DGH | 0.625 mg/l | 0 | 0 | 0 | 0 | 42 | 100 | 100 | 100 | 100 | 100 | 100 |
| DGH | 1.25 mg/l | 0 | 0 | 0 | 100 | 100 | 100 | 100 | 100 | 100 | 100 | 100 |
| DGH | 5.0 mg/l | 0 | 0 | 0 | 100 | 100 | 100 | 100 | 100 | 100 | 100 | 100 |
| MBT | 0.625 mg/l | 0 | 0 | 0 | 17 | 50 | 50 | 67 | 67 | 75 | 75 | 75 |
| MBT | 1.25 mg/l | 0 | 0 | 0 | 92 | 92 | 100 | 100 | 100 | 100 | 100 | 100 |
| MBT | 2.5 mg/l | 0 | 0 | 33 | 100 | 100 | 100 | 100 | 100 | 100 | 100 | 100 |
| MBT | 5.0 mg/l | 0 | 0 | 8 | 58 | 92 | 100 | 100 | 100 | 100 | 100 | 100 |
| MBT:DGH | 6.25 mg/l MBT:.625 mg/l DGH | 0 | 0 | 8 | 75 | 100 | 100 | 100 | 100 | 100 | 100 | 100 |
| MBT:DGH | 3.75 mg/l MBT:.625 mg/l DGH | 0 | 50 | 83 | 100 | 100 | 100 | 100 | 100 | 100 | 100 | 100 |
| MBT:DGH | 2.5 mg/l MBT:.625 mg/l DGH | 0 | 17 | 50 | 83 | 100 | 100 | 100 | 100 | 100 | 100 | 100 |
| MBT:DGH | 3.75 mg/l MBT:1.25 mg/l DGH | 0 | 25 | 33 | 67 | 100 | 100 | 100 | 100 | 100 | 100 | 100 |
| MBT:DGH | 2.5 mg/l MBT:1.25 mg/l DGH | 0 | 58 | 75 | 92 | 92 | 100 | 100 | 100 | 100 | 100 | 100 |
| MBT:DGH | 2.5 mg/l MBT:2.5 mg/l DGH | 0 | 67 | 92 | 100 | 100 | 100 | 100 | 100 | 100 | 100 | 100 |
| MBT:DGH | 1.25 mg/l MBT:2.5 mg/l DGH | 0 | 8 | 50 | 100 | 100 | 100 | 100 | 100 | 100 | 100 | 100 |
| MBT:DGH | .625 mg/l MBT:2.5 mg/l DGH | 0 | 0 | 0 | 75 | 100 | 100 | 100 | 100 | 100 | 100 | 100 |
| MBT:BNS | 2.25 mg/l BNS:1.25 mg/l MBT | 0 | 42 | 75 | 100 | 100 | 100 | 100 | 100 | 100 | 100 | 100 |
| DGH:Quat | 2.0 mg/l Quat:1.25 mg/l DGH | 0 | 0 | 0 | 100 | 100 | 100 | 100 | 100 | 100 | 100 | 100 |
| 24 hr. Exposure Only | | | Latent Response | | | | | | | | | |
| MBT:DGH | 2.5 mg/l MBT:.625 mg/l DGH | 0 | 0 | 0 | 0 | 8 | 25 | 33 | 42 | 67 | 75 | 92 |

DGH = n-dodecylguanidine hydrochloride
MBT = methylene bis-thiocyanate
Quat = n-alkyl (50% $C_{14}$, 40% $C_{12}$, 10% $C_{16}$) dimethyl benzyl ammonium chloride
BNS = beta-bromo-beta-nitrostyrene Static acute bioassays were conducted with a water/ethylene glycol formulation comprised of 8% n-alkyl (50% $C_{14}$, 40% $C_{12}$, 10% $C_{16}$) dimethyl benzyl ammonium chloride (Quat) and 5% n-dodecylguanidine hydrochloride (DGH) using late stage veligers. The concentrations of DGH/Quat formulation examined in each test were 5, 10, 15, 25, and 50 ppm, spanning the application range employed in recirculating and once-through water systems. Boerner glass microslides were used as the test containers. Four replicate slide cells were used with each test solution. Approximately 40 to 60 larvae were distributed into the four replicate cells containing either control diluent or a toxicant solution. The larvae were immediately examined and counted upon being transferred to the cells. Mortality counts were made at 3, 6, 24 and 30 hours during the exposure periods. Mortality counts were corroborated by an independent observer. Mortality was defined as the cessation of cilia and body movements and the necrosis of the body tissues. Microscopic examinations for mortality determinations were made using a compound microscope at 40× to 100× power. During testing, the Boerner microslides were stored in airtight plastic trays above a shallow layer of water to prevent evaporation of the test solutions.

Adult Corbicula, ranging in size from 1 cm to 2.5 cm, were acclimated in the laboratory for several weeks. Adult clams were fed a daily diet of laboratory cultured algae and supplied with fresh diluent water daily. Only a few of the several hundred clams being cultured expired during the acclimation period.

A static bioassay was conducted with the DGH/Quat formulation on the adult clams with examination of concentrations at 5, 10, 15, 25, 50 and 100 ppm. Glass beakers were used as the test containers. Two replicate beakers were used for each test solution. Six adult calms were placed into each of the beakers containing diluent water or toxicant. After the 72 hour exposure period, a recovery period was initiated by transferring the remaining live clams to test vessels with only diluent water. Mortality responses were observed at 24, 30, 48, 54 and 78 hours. Mortality is defined as the point in time when the bivalve shell of the adult clam gapes open from the relaxed muscle tissue of the expired clam. All clams that were not actively siphoning at the end of the recovery period were opened up for microscopic examination to determine their viability or mortality. All clams were confirmed viable by the actively beating cilia lining the gill epithelium.

The diluent water used in testing and culturing was the combined municipal and well water sources which was dechlorinated through activated carbon filtration and heavily aerated. This water is of suitable quality for continuous culture of the Cladoceran species *Daphnia magna* and has been demonstrated to be capable of adequately sustaining the larval clams. During the testing periods, only 2% mortality of the late stage veligers was witnessed in the control groups. The results of the experimental data are summarized in Tables III and IV. The mortality values presented are percentages of the total number of individuals.

TABLE III

Late Veliger Stage Asiatic Clam Larvae
Cumulative Percent Mortality

| Formulation Concentration mg/l | Observation Time (hrs) | | | |
|---|---|---|---|---|
| | 3 | 6 | 24 | 30 |
| 50 | 40% | 57% | 70% | 76% |
| 25 | 7 | 14 | 45 | 52 |
| 15 | 2 | 4 | 25 | 29 |
| 10 | 0 | 0 | 29 | 29 |
| 5 | 0 | 0 | 4 | 4 |
| 0 (control) | 0 | 0 | 2 | 2 |

TABLE IV

Adult Asiatic Clams
Cumulative Percent Mortality

| Formulation Concentration mg/l | Observation Time (hrs) | | | | |
|---|---|---|---|---|---|
| | 24 | 30 | 48 | 54 | 78 |
| 100 | 8% | 33% | 100% | — | — |
| 50 | 0 | 25 | 100 | — | — |
| 25 | 0 | 0 | 75 | 100% | — |
| 15 | 0 | 0 | 42 | 58 | 100% |
| 10 | 0 | 0 | 0 | 50 | 100 |
| 5 | 0 | 0 | 0 | 0 | 75 |
| 0 (control) | 0 | 0 | 0 | 0 | 0 | actives and combined actives to adult clams after being exposed to formulations for a period of 24 hours. Glass 5-liter aquaria containing culture dishes were used as the test vessels. Two replicate aquaria were used for each test solution. Ten adult Corbicula were placed into each of the tanks containing the diluent water or test solution. After the 24 hour exposure period with the test solutions, all solutions were emptied and thoroughly flushed with diluent water to commence the examination period for latent efficacy response. Each aquarium was flushed twice each day. A daily food supplement (15 ml aliquot of an algal culture) was provided to each vessel starting 24 hours after the exposure period. Latent efficacy responses were recorded for more than 200 hours following the 24 hour exposures. Results are reported in Tables V and VI.

The results reported in Tables V and VI demonstrate the significant latent efficacy responses that result from this invention to adult clams after being exposed to the formulations for a period of only 24 hours. This latent efficacy response usually does not commence until 2 to 6 days following the application period.

EXAMPLE 5

A field trial was conducted using a water/ethylene glycol formulation comprised of 8% n-alkyl (50% $C_{14}$, 40% $C_{12}$, 10% $C_{16}$) dimethyl benzyl ammonium chloride (Quat) and 5% n-dodecylguanidine hydrochloride (DGH) for exterminating mollusks (primarily Asiatic clams) that were colonizing the intake bays at a Texas utilities generating plant.

TABLE V

| | | Cumulative % Mortality | | | | | | | | | | | |
|---|---|---|---|---|---|---|---|---|---|---|---|---|---|
| | | | | | | | Latent Response | | | | | | |
| Actives | Total Active Concentration | 24 Hr. | 48 Hr. | 72 Hr. | 77 Hr. | 96 Hr. | 120 Hr. | 144 Hr. | 152 Hr. | 168 Hr. | 185 Hr. | 211 Hr. | 235 Hr. |
| Control | | 0 | 0 | 0 | 0 | 0 | 0 | 0 | 0 | 0 | 0 | 0 | 0 |
| DGH:Quat | 2.0 mg/l Quat: 1.25 mg/l DGH | 0 | 0 | 15 | 55 | 95 | 100 | — | — | — | — | — | — |
| DGH:Quat | 4.0 mg/l Quat: 2.5 mg/l DGH | 0 | 0 | 65 | 100 | — | — | — | — | — | — | — | — |
| MBT | 2.5 mg/l MBT | 0 | 0 | 0 | 0 | 0 | 10 | 45 | 65 | 95 | 100 | — | — |
| Quat | 2.5 mg/l Quat | 5 | 5 | 10 | 35 | 95 | 100 | — | — | — | — | — | — |
| DGH | 2.5 mg/l DGH | 0 | 0 | 15 | 20 | 90 | 100 | — | — | — | — | — | — |
| MBT:DGH | 2.5 mg/l MBT: .625 mg/l DGH | 0 | 0 | 0 | 0 | 0 | 5 | 5 | 10 | 25 | 35 | 45 | 60 |
| MBT:DGH | 2.5 mg/l MBT: 2.5 mg/l DGH | 0 | 0 | 0 | 0 | 5 | 20 | 45 | 65 | 90 | 95 | 95 | 95 |

TABLE VI

| | | Cumulative % Mortality | | | | | | | | | | | |
|---|---|---|---|---|---|---|---|---|---|---|---|---|---|
| | | | | | | | Latent Response | | | | | | |
| Actives | Total Active Concentration | 24 Hr. | 48 Hr. | 72 Hr. | 96 Hr. | 100 Hr. | 153 Hr. | 168 Hr. | 173 Hr. | 196 Hr. | 221 Hr. | 245 Hr. | 332 Hr. |
| Control | | 0 | 0 | 0 | 0 | 0 | 0 | 0 | 0 | 0 | 0 | 0 | 0 |
| MBT:BNS | 2.25 mg/l BNS: 1.25 mg/l MBT | 0 | 0 | 0 | 0 | 0 | 0 | 0 | 0 | 0 | 0 | 0 | 0 |
| DGH:Quat | 2.0 mg/l Quat: 1.25 mg/l DGH | 0 | 0 | 15 | 90 | 90 | 95 | 95 | 95 | 95 | 95 | 95 | 95 |
| MBT:DGH | 2.5 mg/l MBT: .625 mg/l DGH | 0 | 0 | 0 | 0 | 0 | 10 | 20 | 25 | 40 | 50 | 60 | 60 |
| MBT:DGH | 2.5 mg/l MBT: 2.5 mg/l DGH | 0 | 0 | 5 | 5 | 5 | 25 | 70 | 75 | 85 | 95 | 95 | 95 |
| MBT:DGH | 1.25 mg/l MBT: 2.5 mg/l DGH | 0 | 0 | 0 | 0 | 0 | 0 | 5 | 5 | 5 | 5 | 5 | 5 |

EXAMPLE 4

Laboratory studies were conducted to examine the latent efficacy responses that result from the individual Two non-operating intake bays were used for the field trial evaluations. Intake bay 1B received four 60 ppm shot feed applications during a 48 hour exposure period, while intake bay 2B received two 60 ppm shot feed applications during a 24 hour exposure period. It should be noted that the 60 ppm applications represent only the overall application based upon the volume of water in the bay and not the localized concentrations. In fact, localized concentrations were expected to be higher at the lower water depths as demonstrated by the efficacy results with water depth. All applications were applied with the aid of a sparge pipe positioned at the bottom of each bay. Both bays were flushed with fresh water with fresh lake water. Table VII provides the results of the biomonitoring.

2. One of the stationary screens in bay 1B, positioned behind the traveling screen, was cleared of all clams residing on the ledges of the screen. Every other 3 foot ledge was then reseeded with a total of 75 mollusks and the stationary screen was lowered back into the bay. The mollusks were examined daily until 5 days following treatment. The results are reported in Table VIII.

TABLE VII

| | Total Number of Dead Mollusks* Per Period/Cumulative % Mortality | | | | | | | |
|---|---|---|---|---|---|---|---|---|
| | Days After Last Application/Time of Observation | | | | | | | |
| | 0 2:00 PM | 1 9:00 AM | 1 1:00 PM | 1 7:30 PM | 2 2:00 PM | 3 9:30 AM | 4 9:30 AM | 4 3:00 PM |
| Control | 0/0% | 0/0% | 0/0% | 0/0% | 0/0% | 0/0% | 5/2% | 2/3% |
| Intake Bay 1B West (Lake Side) | 24/12% | 81/52% | 29/66% | 53/92% | 16/100% | | | |
| Intake Bay 1B East (Plant Side) | 43/6% | 633/95% | 23/98% | 10/99% | 2/99% | 2/100% | | |

| | Days After Last Application/Time of Observation | | | | | | | |
|---|---|---|---|---|---|---|---|---|
| | 1 2:00 PM | 2 10:00 AM | 2 7:45 PM | 3 9:00 AM | 3 2:30 PM | 3 6:30 PM | 4 9:30 AM | 4 3:00 PM |
| Intake Bay 2B West (Lake Side) | 47/30% | 9/46% | 45/88% | 11/97% | 3/100% | | | |
| Intake Bay 2B East (Plant Side) | 0/0% | 0/0% | 0/0% | 3/2% | 49/30% | 4/32% | 14/41% | 39/63% |

*Mollusks include primarily Asiatic clams and a few fresh water mussels and snails.

TABLE VIII

| | Total Number of Dead Mollusks* Per Period/ Cumulative % Mortality (Minimum Estimation) | | | | | |
|---|---|---|---|---|---|---|
| Observation Time: Days Following Treatment | Intake Bay Depth (ft) | | | | | |
| | 37' | 31' | 25' | 19' | 13' | 7' |
| 0 | 66/88% | 0/0% | 0/0% | 0/0% | 0/0% | 0/0% |
| 1 | 2/91% | 27/36% | 17/23% | 0/0% | 0/0% | 0/0% |
| 2 | 2/93% | 20/63% | 26/57% | 1/1% | 0/0% | 0/0% |
| 3 | 4/99% | 11/77% | 23/88% | 3/5% | 0/0% | 0/0% |
| 4 | 1/100% | 3/81% | 9/100% | 4/11% | 0/0% | 0/0% |
| 5 | — | 3/85% | — | 2/15% | 0/0% | 1/1% |

*Mollusks include Asiatic clams and fresh water mussels.

following the exposure periods. Treatments were monitored during and after the exposure period as follows:

1. Treated water collected from 40 foot depth locations on the east and west sides of both bays were transferred to aquaria containing mollusks. The mollusks were collected from the intake bays using a dredge prior to the treatments. Each aquarium was flushed with freshly treated water at ½ hour and 3 hours following each shot feed application. Following the exposure period, each aquarium was flushed 2 to 3 times a day 3. Dredge samples containing mollusks were collected from the treated bays and transferred to aquaria for monitoring latent efficacy responses. The aquaria were flushed 2 to 3 times daily with lake water during a period of 4 days following the applications. Monitoring the dredge samples was not continued beyond 4 days because of a significant clam mortality that occurred in the control tank on the next day. The control mortality may have been a result of either significant temperature and/or pH fluctuations of the lake water. The results are reported in Table IX.

TABLE IX

| | Total Number of Dead Mollusks* Per Period/Cumulative % Mortality | | | | | | | |
|---|---|---|---|---|---|---|---|---|
| | Days After Last Application/Time of Observation | | | | | | | |
| | 1 1:00 PM | 1 8:00 PM | 2 9:00 AM | 2 2:30 PM | 2 6:30 PM | 3 9:30 AM | 3 3:00 PM | 4 9:30 AM |
| Control | 0/0% | 0/0% | 0/0% | 0/0% | 0/0% | 0/0% | 0/0% | 5/2% |
| Intake Bay 1B | 31/54% | 12/74% | 2/79% | 1/80% | 1/82% | 0/82% | 0/82% | — |

| | Days After Last Application/Time of Observation | | | | | |
|---|---|---|---|---|---|---|
| | 2 8:00 PM | 3 9:00 AM | 3 2:00 PM | 3 6:30 PM | 4 9:30 AM | 4 3:00 PM |
| Intake Bay 2B (Dredge Sample #1) | 50/15% | 36/25% | 24/32% | 31/41% | 55/58% | 26/66% |
| Intake Bay 2B | 95/9% | 94/18% | 41/21% | 17/23% | 72/30% | 49/34% |

TABLE IX-continued

Total Number of Dead Mollusks* Per Period/Cumulative % Mortality (Dredge Sample #2)

*Mollusks were primarily Asiatic clams.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What we claim is:

1. A method for controlling the fouling potential of mollusks in an aqueous system of the type prone to such fouling, which comprises adding to said system an effective amount to control said mollusk-based fouling of a water soluble alkyl guanidine salt compound wherein the alkyl group has from about 8 to 18 carbon atoms.

2. A method as recited in claim 1, wherein said mollusks are Asiatic clams.

3. A method as recited in claim 2 wherein said aqueous system is the aqueous system of a cooling water system.

4. A method as recited in claim 1 wherein said water soluble alkyl guanidine salt is n-dodecylguanidine hydrochloride.

5. A method as recited in claim 4 further comprising adding an effective amount of an alkyl dimethyl benzyl ammonium chloride having an alkyl chain length from $C_6$ to $C_{24}$ to said aqueous system in combination with said water soluble alkyl guanidine salt compound for controlling the mollusk-based fouling.

6. A method as recited in claim 5 wherein said alkyl dimethyl benzyl ammonium chloride is n-alkyl (40% $C_{12}$, 50% $C_{14}$, and 10% $C_{16}$) dimethyl benzyl ammonium chloride.

7. A method as recited in claim 4, further comprising adding methylene bis thiocyanate to said aqueous system.

8. A method as recited in claim 1, wherein said mollusks are comprised primarily of Corbicula.

9. A method according to claim 8 wherein said aqueous system is the aqueous system of a cooling water system.

10. A method for controlling the fouling potential of mollusks in an aqueous system of the type prone to such fouling, said method comprising feeding an effective amount of a water soluble alkyl guanidine salt compound wherein the alkyl group has from about 8 to 18 carbon atoms, for an effective period of time, such that said compound will kill at least a portion of said mollusks for some time after discontinuance of said feed.

11. A method as recited in claim 10 wherein said mollusks are Asiatic clams.

12. A method as recited in claim 11 wherein said aqueous system is the aqueous system of a cooling water system.

13. A method as recited in claim 10 wherein said water soluble alkyl guanidine salt is n-dodecylguanidine hydrochloride.

14. A method as recited in claim 13 further comprising adding an effective amount of an alkyl dimethyl benzyl ammonium chloride having an alkyl chain length from $C_6$ to $C_{24}$ to said aqueous system in combination with said water soluble alkyl guanidine salt compound for controlling the macrofouling.

15. A method as recited in claim 14 wherein said alkyl dimethyl benzyl ammonium chloride is n-alkyl (40% $C_{12}$, 50% $C_{14}$ and 10% $C_{16}$) dimethyl benzyl ammonium chloride.

16. A method as recited in claim 13 further comprising adding methylene bis thiocyanate to said aqueous system.

17. A method as recited in claim 10 wherein said mollusks are comprised primarily of Corbicula.

18. A method as recited in claim 17 wherein said aqueous system is the aqueous system of a cooling water system.

19. A method for controlling the fouling potential of mollusks in an aqueous system of the type prone to such fouling, which comprises adding to said system an effective amount to control said mollusk-based fouling of a water soluble alkyl guanidine salt compound wherein the alkyl group has from about 8 to 18 carbon atoms and said water soluble alkyl guanidine salt is capable of killing at least a portion of said mollusks within a 72-hour period after an initial exposure to said compound of up to about 24 hours.

20. A method as recited in claim 19 wherein said mollusks are Asiatic clams.

21. A method as recited in claim 20 wherein said aqueous system is the aqueous system of a cooling water system.

22. A method as recited in claim 19 wherein said water soluble alkyl guanidine salt is n-dodecylguanidine hydrochloride.

23. A method as recited in claim 22 further comprising adding an effective amount of an alkyl dimethyl benzyl ammonium chloride having an alkyl chain length from $C_6$ to $C_{24}$ to said aqueous system in combination with said water soluble alkyl guanidine salt compound for controlling the macrofouling.

24. A method as recited in claim 23 wherein said alkyl dimethyl benzyl ammonium chloride is n-alkyl (40% $C_{12}$, 50% $C_{14}$ and 10% $C_{16}$) dimethyl benzyl ammonium chloride.

25. A method as recited in claim 22 further comprising adding methylene bis thiocyanate to said aqueous system.

26. A method as recited in claim 19 wherein said mollusks are comprised primarily of Corbicula.

27. A method as recited in claim 26 wherein said aqueous system is the aqueous system of a cooling water system.

* * * * *

UNITED STATES PATENT AND TRADEMARK OFFICE
CERTIFICATE OF CORRECTION

PATENT NO. : 4,906,385
DATED : March 6, 1990
INVENTOR(S) : Lyons et al

It is certified that error appears in the above-identified patent and that said Letters Patent is hereby corrected as shown below:

ON TITLE PAGE:

Item [*] should read as follows:

The portion of the term of this patent subsequent to March 28, 2006 has been disclaimed.

Signed and Sealed this

Third Day of December, 1991

Attest:

HARRY F. MANBECK, JR.

*Attesting Officer*    *Commissioner of Patents and Trademarks*